US006847915B2

(12) United States Patent
Liang et al.

(10) Patent No.: US 6,847,915 B2
(45) Date of Patent: Jan. 25, 2005

(54) CONTACTED THREE DIMENSIONAL SOLE MEASURER

(75) Inventors: Jianxiong Liang, Tsuen Wan (HK); Zhiqiang Liang, Tsuen Wan (HK); Shaorong Feng, Tsuen Wan (HK)

(73) Assignee: Ultrafoot Hong Kong Ltd., Tsuen Wan (HK)

( * ) Notice: Subject to any disclaimer, the term of this patent is extended or adjusted under 35 U.S.C. 154(b) by 0 days.

(21) Appl. No.: 10/391,891

(22) Filed: Mar. 18, 2003

(65) Prior Publication Data

US 2004/0186682 A1 Sep. 23, 2004

(30) Foreign Application Priority Data

Jun. 10, 2002 (CN) ........................... 02270909 U

(51) Int. Cl.⁷ .............................................. G01B 15/00
(52) U.S. Cl. ........................... 702/155; 33/3 A; 33/3 R
(58) Field of Search ............................... 702/155–158, 702/162; 33/3 A, 3 R

(56) References Cited

FOREIGN PATENT DOCUMENTS

JP 403247304 A * 11/1991 ............ A43D/1/02

* cited by examiner

*Primary Examiner*—John Barlow
*Assistant Examiner*—Meagan S Walling
(74) *Attorney, Agent, or Firm*—Donn K. Harms

(57) ABSTRACT

The disclosed device features is a contacting three dimensional sole measuring device to produce accurate three dimensional renditions of the bottom of a human foot placed thereon. The device features one or a plurality of sensors groups communicating with the top surface of a case. Each sensor group is dimensioned to accommodate the area of a footprint of a human foot when placed on top of it. Each sensor group is composed of a plurality of linear displacement sensors which measure the displacement caused by the bottom surface of the foot and communicate that displacement to a data processing device which compiles a three dimensional rendition of the bottom of the foot surface from the individual data points from the displacement senors. Accurate renditions of the bottom surface of a human foot may be achieved by a person simply standing on the sensor groups barefoot.

11 Claims, 2 Drawing Sheets

CONTACTED THREE DIMENSIONAL SOLE MEASURER

FIELD OF THE INVENTION

This application claims the benefit of PRC Application No. 02270909.6 filed Jun. 10, 2002. The disclosed device relates to sole measuring equipment for measuring the soles of the feet. More particularly it relates to a device which when contacting the feet of a human standing upon it will provide a three dimensional (3D) sole measurement.

BACKGROUND OF THE INVENTION

The foot is a very important part of the human body. However, because of physiology causes, many people's feet will become distorted after years of walking. The worst of such can even become malformed. Such distortion and malformation can bring about pain and inconvenience in walking and also result in inappropriate standing posture. The device herein disclosed taking into account the importance of feet in human movement, applies high technology illumination methods to measure human foot shapes by rectifying the biologic power line to plumb centrally. Such precise measurements can assist in the manufacture of footwear that allows children's feet and foot skeleton to develop normally and preventing and remedying tarsoptosis more commonly know as "flat feet". The disclosed device also provides for developing physiological movement analysis which will arouse worldwide attention.

The device when employed provides a great advance in the medical care and podiatry industry through the provision of the ability for the precise measurement of feet. Using such heretofore hard to obtain measurements will allow a broadening and great improvement in the production of medical care and footwear products for feet.

Prior art such as Chinese patent number of ZL 98245724.3 for Non-Contacted Sole Scanner, achieves a foot scan through laser scan groupware get the 3 dimension data of the foot. However, with weakness of low measuring precision, unstable results, complex structure and requiring facilities for people to lie down so that the measurer can take the data, this device cannot work effectively in obtaining data.

SUMMARY OF THE INVENTION

The herein disclosed device is designed to provide a foot contacted or contacting three dimensional sole measurer that is simply structured, convenient and quick to use, and provides a high degree of measuring precision and constantly accurate results.

The disclosed device features a case, a power outlet at the bottom of the case, a few requisite circuit boards inside the case, three layers of uninstall boards in the middle of it, and sensor groups vertically installed on the uninstall boards to provide data points produced from lateral translation of a foot placed thereon. The sensor groups are rectangle lattices composed of linear displacement sensors. The spacing of these sensors center axis is in the current best mode substantially equal to or less than 15 mm however those skilled in the art will no doubt realize that other spacings can be used depending on the purpose intended and accuracy desired and such are anticipated. The circuit boards inside the case are equipped with data gathering instruments and data handling instruments to record the displacement of the linear displacement sensors to thereby achieve an electronic three dimensional footprint.

The disclosed device herein is simply structured and convenient to use. Because the output capacity of linear displacement sensors forms a linear relation with mechanical displacement, when a person steps on the rectangle lattices of sensors, his foot causes a linear displacement, and the counterpoints of the rectangle lattices of sensors output a discretely analog signal of data points of the amount of displacement of each sensor contacting the bottom of the foot.

After data gathering, the acquired data may be changed into numerical quantity, and the discretely analog data from each individual senor recording its individual displacement is converted into three dimensional drawings after data processing by the electrical components of the device or a communicating device adapted to receive the data and render the three dimensional footprint. As such, the disclosed device can recognize the displacement of each of the displacement sensors, interpret that data into three dimensional footprint drawings, and achieve a higher measuring precision and more stable result than conventionally used foot measuring devices.

BRIEF DESCRIPTION OF THE DRAWINGS

The following associative attached drawings are a further description of this utilized new pattern.

DETAILED DESCRIPTION OF PREFERRED EMBODIMENTS

Figure 1:
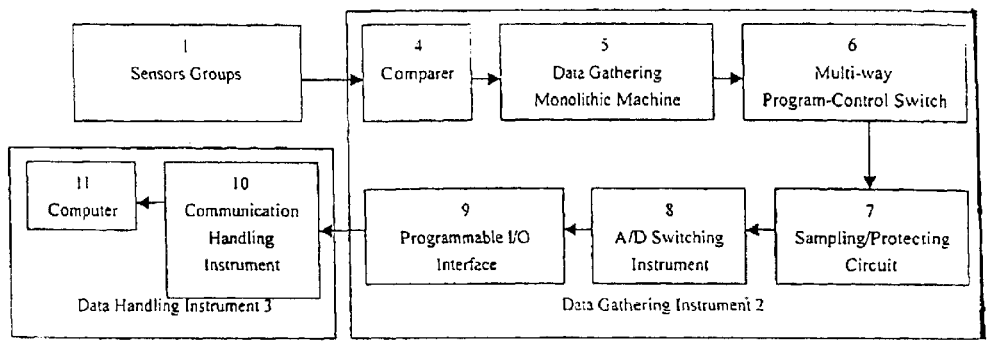
FIG. 1 is Circuit Frame Drawing of this utilized new pattern.
Figure 2:
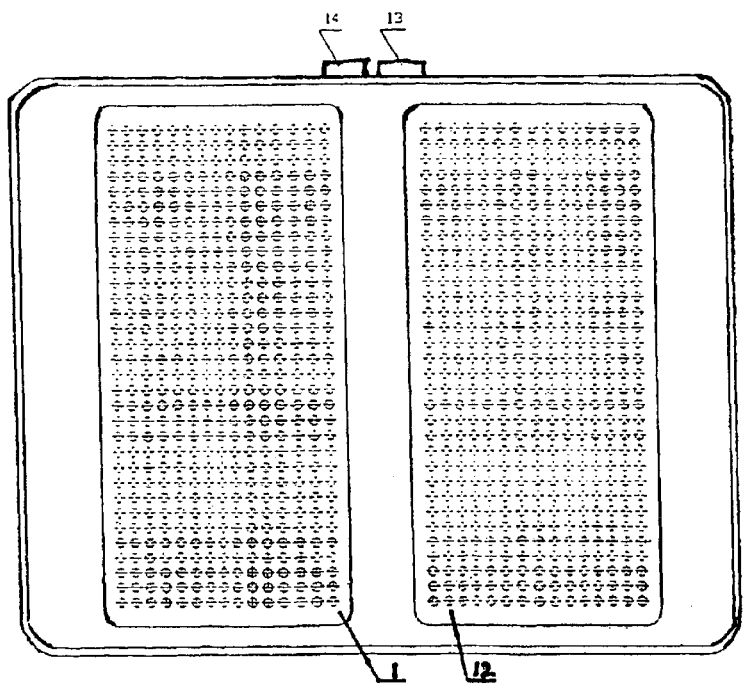
FIG. 2 is Plan form/Vertical View of this utilized new pattern.
Figure 3:
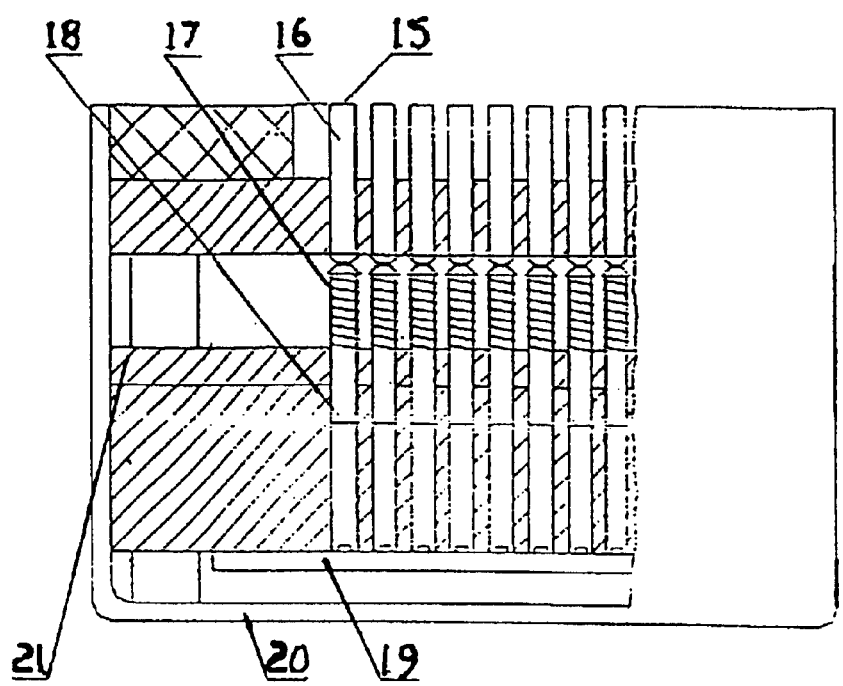
FIG. 3 is A—A Cutaway View of FIG. 2.

As shown in the accompany drawings 1–3, the disclosed device is composed of a case (20), a power outlet (14) and data interface (13) at a sidewall of the case (20). A number of circuit boards (19) are located inside the case (20) for receiving data from the individual lateral displacement sensors which communicate with the top surface of the case. Three uninstall boards (21) are located in the middle of the case (20). The sensor groups (1) are vertically installed on the uninstall boards (21).

The sensor groups (1) are placed on the case (2) to form at least one and preferably two, rectangle lattices or sensor groups of touch heads (15) arranged upright which communicate with the top surface and communicate their linear displacement with linear displacement sensors (12). The spacing apart of the center axis of the plurality linear displacement sensors (12) making up the sensor groups is currently best at substantially equal to or less than 15 mm. The spacing is equidistantly distributed on each rectangle lattice forming the sensor group of linear displacement sensors (12) which in the current best mode covers substantially an area of 150 mm×310 mm which should accommodate most foot sizes.

In use, when a bare footed or sock footed person steps on surveying area in the latices formed of linear displacement sensors (12), their weight transmitted to the bottom of their foot will translate the displacement sensors (12) which will output a displacement signal at various data points according to the amount of displacement caused by the shape of the bottom of the foot. Consequently each different foot will yield a different sole shape which is highly accurate due to the numerous contacts with the foot producing numerous data points which render the lateral translation caused by the foot surface and thus its shape or contour. Data from the individual data points is communicated to a means for data processing which therein renders a three dimensional rendition of the foot surface using video or printing or other means to render the foot surface.

As shown in the current best embodiment, the circuit board (19) is equipped with data gathering instrument (2) and data handling instrument (3). The data gathering instrument (2) is made up of comparer (4), data gathering monolithic machine (5), multi-way program-controlled switch (6), sampling/protecting circuit (7), A/D switching instrument (8) and programmable I/O interface (9). When sensor groups (1) pass the displacement discretely analog quantity to comparer (4), it is passed through data gathering monolithic machine (5), multi-way program-controlled switch (6) and sampling/protecting circuit (7). A/D switching instrument (8) turns the displacement data into numerical quantity, and then the programmable data interface (9) passes the numerical quantity to data handling instrument (3).

The Data handling instrument (3) is composed of a communication handling instrument (10) and external-deposited computers (11) that operatively communicate through a data transferring interface (13). The communication handling instrument (10) simultaneously converts the communicated numerical quantity into three dimension drawings, and transfers them to a means for data processing such as computers (11) to read out various data and drawings which can be viewed, stored, printed, or otherwise used.

Means for measurement of the linear displacement caused by the footprint of the user is provided by linear displacement sensors (12) in the current best mode would feature measurements by capacitance, optical, or grating sensors which measure lateral translation and transform the mechanical displacement to electrical values. They is made up of touch heads (15), guide plate (16), springs (17), and displacement-optical signal transforming instruments (18). Linear displacement sensors (12) can also be of capacitive-crib form (~=). Of course those skilled in the art will realize that other means to collect and process the data points produced by the lateral translation of the individual sensors can be used to render the surface contours of the foot and such is anticipated.

While all of the fundamental characteristics and features of the disclosed device herein have been shown and described, it should be understood that various substitutions, modifications, and variations may be made by those skilled in the art without departing from the spirit or scope of the invention. Consequently, all such modifications and variations are included within the scope of the invention as herein disclosed in drawings and other enclosures and defined by the following claims.

What is claimed is:

1. A contacting three dimensional sole measurer comprising:
   a case having a sidewall and a top surface;
   at least one sensor group located communicating with said top surface, said sensor group dimensioned to accommodate the area of a footprint of a human foot placed thereon;
   said sensor group having a plurality of means to sense linear displacement caused by the surface of said foot placed thereon each said means to sense linear displacement having, a touch head having a first end adjacent to said top surface and having a second end opposite said first end, said touch head laterally translatable in within a guide, toward and away from said top surface; a biasing means to bias said touch head toward said top surface; and means to sense lateral translation of said touch head a distance away from said top surface and communicate said distance in an electrical signal to said data processing means when said touch head is translated by said foot placed thereon;
   each of said plurality of means to sense linear displacement communicating displacement values at individual points of reference, to a to means for data processing; and
   said means for data processing thereby rendering a three dimensional rendition of said surface of said foot placed on said sensor group using said displacement values from said plurality of means to sense linear displacement.

2. The contacting three dimensional sole measurer of claim 1 wherein said means to sense lateral translation of said touch head comprises:
   optical sensor means for sensing the distance of lateral translation of said second end of said touch head away from said top surface.

3. The contacting three dimensional sole measurer of claim 1 wherein said means to sense the distance of lateral translation of said touch head comprises:
   capacitance sensor means for sensing lateral translation of said touch head away from said top surface.

4. The contacting three dimensional sole measurer of claim 1 wherein said means to sense the distance of lateral translation of said touch head comprises:
   grating sensor means for sensing lateral translation of said touch head away from said top surface.

5. The contacting three dimensional sole measurer of claim 1 wherein said plurality of means to sense linear displacement which populate said sensor group are spaced from each other substantially 15 mm apart.

6. The contacting three dimensional sole measurer of claim 5 wherein the total lateral translation of said of means to sense linear displacement is substantially 4 mm.

7. The contacting three dimensional sole measurer of claim 5 wherein said sensor group is rectangular in shape and said area of said footprint is substantially 150 mm×310 mm.

8. The contacting three dimensional sole measurer of claim 1 wherein said touch heads populate said sensor group spaced from each other substantially 15 mm apart.

9. The contacting three dimensional sole measurer of claim 8 wherein the total lateral translation of said of means to sense linear displacement is substantially 4 mm.

10. The contacting three dimensional sole measurer of claim 1 wherein said sensor group is rectangular in shape and said area of said footprint is substantially 150 mm×310 mm.

11. The contacting three dimensional sole measurer of claim 1 wherein said means for data processing comprises:
    a comparer receiving electronic signals representing lateral translation from each of said means to sense linear displacement;
    a data gathering monolithic machine receiving data from said comparer;
    a multi-way program-controlled switch receiving data from said data gathering monolithic machine;
    a sampling/protecting circuit receiving data from said multi-way program-controlled switch;
    an A/D switching instrument for receiving data communicated from said sampling/protecting circuit;
    a programmable I/O interface for receiving data from said A/D switching instrument; and
    means for communication of data from said I/o interface to a computer having software therein adapted to produce said three dimensional rendition.

* * * * *